United States Patent
Pahk et al.

(10) Patent No.: US 12,251,583 B2
(45) Date of Patent: Mar. 18, 2025

(54) CAVITATION BASED TISSUE REMOVAL DEVICE USING FOCUSED ULTRASOUND

(71) Applicant: KOREA INSTITUTE OF SCIENCE AND TECHNOLOGY, Seoul (KR)

(72) Inventors: Ki Joo Pahk, Seoul (KR); Jeong Min Heo, Seoul (KR); Jun Hong Park, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 325 days.

(21) Appl. No.: 17/828,041

(22) Filed: May 31, 2022

(65) Prior Publication Data

US 2022/0387826 A1     Dec. 8, 2022

(30) Foreign Application Priority Data

Jun. 4, 2021 (KR) .................. 10-2021-0072760

(51) Int. Cl.
*A61N 7/02*     (2006.01)
*A61B 8/00*     (2006.01)
(Continued)

(52) U.S. Cl.
CPC .................. *A61N 7/02* (2013.01); *A61B 8/08* (2013.01); *A61B 8/461* (2013.01); *A61N 2007/0008* (2013.01); *A61N 2007/0047* (2013.01)

(58) Field of Classification Search
None
See application file for complete search history.

(56) References Cited

U.S. PATENT DOCUMENTS

2012/0259250 A1* 10/2012 Sapozhnikov ............ A61B 8/00
                                                           601/2
2015/0374342 A1    12/2015 Son et al.
(Continued)

FOREIGN PATENT DOCUMENTS

CN     104013444 A  *  9/2014  ............... A61N 7/02
EP        2403601 B1     5/2016
(Continued)

OTHER PUBLICATIONS

Spencer A. Brown et. al., "Characterization of Nonthermal Focused Ultrasound for Noninvasive Selective Fat Cell Disruption (Lysis): Technical and Preclinical Assessment," Plastic and Reconstructive Surgery, 2009, pp. 92-101, vol. 124, No. 1.
(Continued)

*Primary Examiner* — Joseph M Santos Rodriguez
*Assistant Examiner* — Tommy T Ly
(74) *Attorney, Agent, or Firm* — CANTOR COLBURN LLP

(57) ABSTRACT

The tissue removal device using focused ultrasound includes a focused ultrasound output unit, a mode setting unit to set an output mode of the focused ultrasound, and a control unit to control output characteristics of the focused ultrasound according to the set mode, wherein the output mode is selected from a first mode for removing a tissue in a local area using a vapor bubble formed by the focused ultrasound, a second mode for removing a tissue in a narrower area than the first mode by controlling the output characteristics of the focused ultrasound immediately after the vapor bubble is formed by the focused ultrasound, and a third mode for obtaining a skin tightening effect by generating heating in a subcutaneous fat layer using focused ultrasound of lower intensity and a longer pulse length than the first mode and the second mode.

17 Claims, 16 Drawing Sheets

(51) Int. Cl.
*A61B 8/08* (2006.01)
*A61N 7/00* (2006.01)

(56) References Cited

U.S. PATENT DOCUMENTS

| | | | | |
|---|---|---|---|---|
| 2016/0236013 | A1* | 8/2016 | Carol | A61B 18/04 |
| 2017/0232277 | A1* | 8/2017 | Hall | A61N 7/02 |
| | | | | 601/2 |
| 2018/0064963 | A1 | 3/2018 | Bujak | |
| 2019/0143149 | A1* | 5/2019 | Sverdlik | B06B 1/0622 |
| | | | | 601/2 |
| 2020/0078608 | A1* | 3/2020 | Maxwell | A61B 8/0866 |
| 2020/0164231 | A1* | 5/2020 | Cannata | A61B 34/30 |
| 2021/0008394 | A1* | 1/2021 | Cain | A61N 7/00 |
| 2021/0038135 | A1* | 2/2021 | Chevillet | A61B 5/4836 |
| 2022/0249876 | A1* | 8/2022 | Krone | A61B 8/4411 |

FOREIGN PATENT DOCUMENTS

| | | | | |
|---|---|---|---|---|
| KR | 10-2012-0116908 A | 10/2012 | | |
| KR | 10-1332791 B1 | 11/2013 | | |
| KR | 10-2014-0107846 A | 9/2014 | | |
| KR | 20160139516 A * | 5/2015 | | A61N 7/00 |
| KR | 10-2017-0027652 A | 3/2017 | | |
| KR | 10-2017-0118746 A | 10/2017 | | |
| KR | 10-2018-0100925 A | 9/2018 | | |
| KR | 10-2245150 B1 | 4/2021 | | |
| WO | WO-2008144274 A2 * | 11/2008 | | A61N 7/02 |
| WO | 2011/041234 A1 | 4/2011 | | |
| WO | 2016/118595 A1 | 7/2016 | | |

OTHER PUBLICATIONS

Ki Joo Pahk et al., "Numerical and Experimental Study of Mechanisms Involved in Boiling Histotripsy," Ultrasound in Medicine & Biology, pp. 2848-2861, 2017, vol. 43, No. 12.

Ki Joo Pahk et al., "Mechanical damage induced by the appearance of rectified bubble growth in a viscoelastic medium during boiling histotripsy exposure," Ultrasonics-Sonochemistry, 2019, pp. 164-177, vol. 53.

Ki Joo Pahk et al., "Bubble Dynamics in Boiling Histotripsy," Ultrasound in Medicine & Biology, 2018, 24 pages, vol. 44, No. 12.

* cited by examiner

CAVITATION BASED TISSUE REMOVAL DEVICE USING FOCUSED ULTRASOUND

CROSS-REFERENCE TO RELATED APPLICATION

This application claims priority to Korean Patent Application No. 10-2021-0072760, filed on Jun. 4, 2021, and all the benefits accruing therefrom under 35 U.S.C. § 119, the contents of which in its entirety are herein incorporated by reference.

BACKGROUND

1. Field

The present disclosure relates to a tissue removal device using focused ultrasound, and more particularly, to a device for removing tissues in a local area through vibration of vapor bubbles formed by thermal energy of focused ultrasound.

DESCRIPTION OF GOVERNMENT-FUNDED RESEARCH AND DEVELOPMENT

This research is conducted by Korean Institute of Science and Technology and funded by the Individual Fundamental Research (R&D) Program—Research and development of next-generation non-invasive pressure modulated focused ultrasound surgical technology capable of micro-mechanical ablation of tumor via precise control of cavitation (project serial number: 1711131951) in the Ministry of Science and ICT.

2. Description of the Related Art

To conduct therapy that mitigates a patient's pain or stimulates nerve cell in a specific human body part, a method that inserts electrodes into the patient's human body has been used, but this method may cause damage to the human body in the mechanical invasion process.

Recently, ultrasound stimulation therapy that can stimulate an affected part without a mechanical invasion process is widely used. Ultrasound may be classified into high intensity focused ultrasound (HIFU) and low intensity focused ultrasound (LIFU) according to the intensity, and high intensity focused ultrasound is used for direct treatment, for example, ablation of human body tissues such as cancer cells, tumors and lesions, while low intensity focused ultrasound can obtain medical effects without damaging human body tissues.

The unit of ultrasound intensity is indicated by spatial-peak temporal-average intensity (Ispta) and spatial-peak pulse average intensity (Isppa) according to the Acoustic Output Measurement Standard for Diagnostic Ultrasound Equipment by American Institute for Ultrasound in Medicine and National Electronics Manufacturers Administration (NEMA).

In particular, the use of high intensity focused ultrasound having the Ispta of 3 $W/cm^2$ or above makes it possible to transmit strong acoustic energy that is a few ten to a few hundred times greater than the atmospheric pressure to a target spot in the body, and the transmitted acoustic energy is converted to thermal or mechanical energy, thereby directly removing the tissue.

Thermal energy based high intensity focused ultrasound induces thermal coagulative necrosis of tissue by focusing ultrasonic energy of a predetermined acoustic intensity or above onto a point to generate high temperature at the focal point. This method is being widely used in clinical applications for the purpose of treatment of diseases such as uterine fibroids, adenomyosis, myoma uteri, benign prostatic hyperplasia, prostate cancer, metastatic brain tumor and essential tremor.

Meanwhile, with the change in modern lifestyle and lack of exercise, obesity is increasing all over the world, and there is a significantly increasing interest toward beauty. Accordingly, there is a growing demand for lipolysis that artificially removes adipose tissues in the body. The most widely used invasive lipolysis involves melting adipose tissues by injecting drugs and sucking out the adipose tissues through a sucker to remove them, and there are many side effects such as inflammation of surgical sites during invasion or long recovery and wounds after the surgery.

Recently, techniques for non-invasive removal of adipose tissues using thermal energy of a laser or electromagnetic energy of a radio frequency (RF) signal are being used. However, the method using a laser has difficulties in removing adipose tissues located deep in the body due to the limited energy penetration depth, and the RF method has difficulties in breaking down fats in local areas. Additionally, cryolipolysis is a procedure that eliminates fat cells by fat freezing, and there are less side effects, but it is high-priced and it takes some time (after about 5-12 weeks) to see the effect, and likewise, it fails to break down fats in local areas.

Korean Patent No. 10-1332791 discloses breaking down fats in a non-invasive manner through focused ultrasound-induced cavitation. However, the related art does not specify the method and theory for precisely controlling the output characteristics of focused ultrasound, which makes it difficult to predict the range and extent to which ultrasound breaks down fats and it is impossible to precisely remove only adipose tissues in local areas.

SUMMARY

The present disclosure is directed to providing a device for removing tissues in a local area with high precision by controlling the output characteristics of focused ultrasound according to various modes.

A cavitation based tissue removal device using focused ultrasound according to an embodiment includes a focused ultrasound output unit to output the focused ultrasound, a mode setting unit to set an output mode of the focused ultrasound, and a control unit to control output characteristics of the focused ultrasound according to the set mode, wherein the output mode is selected from a first mode for removing a tissue in a local area using a vapor bubble (i.e., cavitation) formed at an ultrasound focal point position by the focused ultrasound, and a second mode for removing a tissue in a narrower area than the first mode by controlling the output characteristics (for example, the intensity and pulse length of the ultrasound, etc.) of the focused ultrasound immediately after the vapor bubble is formed by the focused ultrasound.

According to an embodiment, the cavitation based tissue removal device using focused ultrasound may further include an ultrasound imaging unit to monitor the formation of the vapor bubble and the tissue, and a display unit to display an ultrasound image acquired using the ultrasound imaging unit.

According to an embodiment, the cavitation based tissue removal device using focused ultrasound may further include a laser pointer for marking the focal point position of the focused ultrasound on a body surface.

According to an embodiment, in the first mode, the focused ultrasound is controlled to have a frequency of 0.1 to 30 MHz, a pulse length of 0.1 to 100 ms, and a pressure of a maximum positive pressure of 40 MPa or above and a maximum negative pressure of −10 MPa or below.

According to an embodiment, in the second mode, the focused ultrasound is outputted in a same pressure intensity condition as the first mode for a predetermined time, and immediately after the vapor bubble is formed, is controlled to have the pulse length of 1 to 100 ms and the pressure of the maximum positive pressure of 40 MPa or below and the maximum negative pressure of −10 MPa or above.

According to an embodiment, the predetermined time during which the focused ultrasound is outputted in the same condition as the first mode may be set between 0.1 and 10 ms.

According to an embodiment, in the condition of the second mode, the focused ultrasound may only form a vapor bubble in the tissue without forming a scattered bubble cloud by a shock scattering effect.

According to an embodiment, in the condition of the second mode, the output characteristics of the focused ultrasound may be at least determined based on biomechanics information, thermodynamics information and bubble dynamics information.

According to an embodiment, the output mode may further include a third mode for tightening a skin without damaging the tissue by generating heating in a subcutaneous fat layer using the focused ultrasound of lower intensity and a longer pulse length than the first mode and the second mode.

According to an embodiment, the tissue may include a fatty tissue or a tumor tissue.

According to an embodiment, the display unit may be configured to display the focal point position of the focused ultrasound on the ultrasound image.

According to an embodiment, the cavitation based tissue removal device using focused ultrasound may further include an ultrasound guide unit to support the focused ultrasound output unit and adjust a penetration depth of the focused ultrasound, a water pump to supply water to a water tube passing through the ultrasound guide unit, and a handle connected to the ultrasound guide unit and equipped with an operation switch for powering on/off the device or selecting the output mode.

According to an embodiment, the cavitation based tissue removal device using focused ultrasound may further include a multi-freedom compact operating system to enable fine tuning of the focal point position of the ultrasound without moving the focused ultrasound output unit, wherein the handle may further include a tuning switch used to fine-tune a position and angle of the focused ultrasound output unit through the multi-freedom compact operating system.

According to an embodiment, the ultrasound guide unit may be customized through 3D printing according to physical structure features of a user.

A method for operating a tissue removal device according to an embodiment of the present disclosure includes receiving an input of selection of an output mode from a user, setting the output mode of focused ultrasound in response to the input, and controlling output characteristics of the focused ultrasound according to the set mode, wherein the output mode may be selected from a first mode for removing a tissue in a local area using a vapor bubble formed by the focused ultrasound, and a second mode for removing a tissue in a narrower area than the first mode by controlling the output characteristics of the focused ultrasound immediately after the vapor bubble is formed by the focused ultrasound.

According to an embodiment, the method for operating a tissue removal device may further include monitoring the formation of the vapor bubble and the tissue using the ultrasound imaging unit, and displaying an ultrasound image acquired through the ultrasound imaging unit on the display unit.

There may be provided a computer program stored in a computer-readable recording medium, the computer program for performing the method for operating a cavitation based tissue removal device using focused ultrasound according to an embodiment.

According to an embodiment of the present disclosure, it is possible to remove tissues in a local area with high precision by controlling the output characteristics of focused ultrasound according to various modes. For example, in the first mode, it is possible to remove tissues in a relatively wide area of a few mm using vapor bubbles and scattering bubble clouds (cavitation clouds) formed by high intensity focused ultrasound satisfying the 'boiling histotripsy' condition, and in the second mode, it is possible to selectively remove only tissues in a narrower area (a few hundred μm to 2 mm) without forming scattering bubble clouds by reducing the ultrasound intensity using pressure modulated focused ultrasound at the moment at which vapor bubbles are formed. The output characteristics (frequency, acoustic pressure, pulse length of ultrasound, etc.) of ultrasound in each mode are determined based on information such as biomechanics information, thermodynamics information and bubble dynamics information, to allow a surgeon to predict the location, size and range of bubbles, thereby achieving precise surgery.

According to a certain embodiment, it is possible to obtain the body tightening effect using thermal energy without cavitation by focused ultrasound of much weaker intensity and longer pulse length than the first mode or the second mode. In addition, it is possible to improve the user convenience using the components for guiding the focal point of ultrasound using a laser pointer or analyzing an image/signal of vapor bubbles and monitoring the tissue removal process in real time by making use of imaging ultrasound.

BRIEF DESCRIPTION OF THE DRAWINGS

The following is a brief introduction to necessary drawings in the description of the embodiments to describe the technical solutions of the embodiments of the present disclosure or the existing technology more clearly. It should be understood that the accompanying drawings are for the purpose of describing the embodiments of the present disclosure and are not intended to be limiting of the present disclosure. Additionally, for clarity of description, some elements in the accompanying drawings may be exaggerated and omitted.

DETAILED DESCRIPTION

Figure 1:
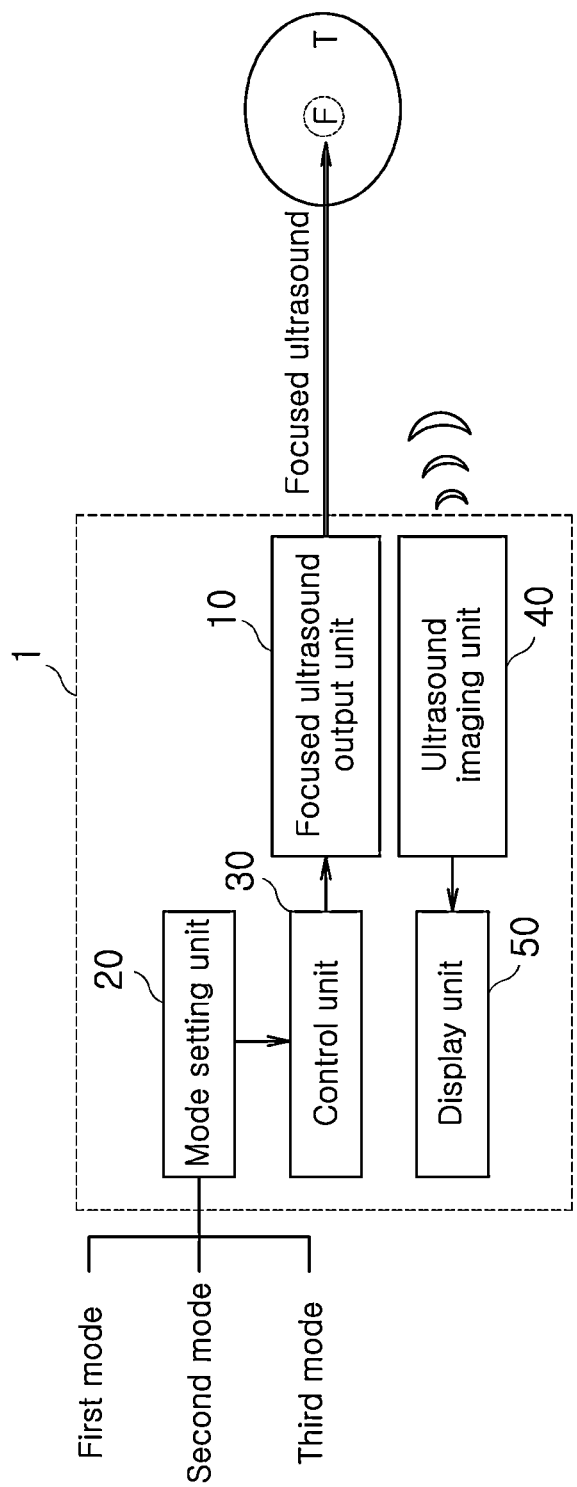
FIG. 1 shows schematically the configuration of a focused ultrasound based tissue removal device that supports a variety of output modes according to an embodiment of the present disclosure.

The following detailed description of the present disclosure is made with reference to the accompanying drawings, in which particular embodiments for practicing the present disclosure are shown for illustration purposes. These embodiments are described in sufficiently detail for those skilled in the art to practice the present disclosure. It should be understood that various embodiments of the present disclosure are different but do not need to be mutually exclusive. For example, particular shapes, structures and features described herein in connection with one embodiment can be embodied in other embodiment without departing from the spirit and scope of the present disclosure. It should be further understood that changes can be made to positions or placement of individual elements in each disclosed embodiment without departing from the spirit and scope of the present disclosure. Accordingly, the following detailed description is not intended to be taken in limiting senses, and the scope of the present disclosure, if appropriately described, is only defined by the appended claims along with the full scope of equivalents to which such claims are entitled. In the drawings, similar reference signs denote same or similar functions in many aspects.

The terms as used herein are general terms selected as those being now used as widely as possible in consideration of functions, but they may vary depending on the intention of those skilled in the art or the convention or the emergence of new technology. Additionally, in certain cases, there may be terms arbitrarily selected by the applicant, and in this case, the meaning will be described in the corresponding description part of the specification. Accordingly, it should be noted that the terms as used herein should be interpreted based on the substantial meaning of the terms and the context throughout the specification, rather than simply the name of the terms.

Hereinafter, exemplary embodiments of a device and method for tissue removal using intensity modulated focused ultrasound will be described in detail with reference to the accompanying drawings.

FIG. 1 shows schematically the configuration of a focused ultrasound based tissue removal device that supports a variety of output modes according to an embodiment of the present disclosure. FIG. 1 shows only necessary elements for describing the present disclosure, and does not depict all essential elements for operating the device or obtaining the effect of the present disclosure. That is, in addition to the disclosed elements, the device may further include elements including a variety of components, modules, devices or software.

Referring to FIG. 1, the tissue removal device 1 according to an embodiment includes a focused ultrasound output unit 10, a mode setting unit 20 to set an output mode of focused ultrasound, a control unit 30 to control the output characteristics of focused ultrasound according to the set mode, an ultrasound imaging unit 40 to monitor the formation of vapor bubbles in tissue, and a display unit 50 to display an ultrasound image.

The focused ultrasound output unit 10 includes an ultrasonic transducer to convert alternating current energy into mechanical vibration. According to an embodiment, the focused ultrasound output unit 10 may include a single transducer or an array of transducers to focus ultrasound onto at least one focal point. The focused ultrasound output unit 10 is configured to receive a control signal that determines the characteristics of ultrasound, for example, acoustic pressure, waveform, frequency and pulse length from the control unit 30, and output the ultrasound of the characteristics according to a set value.

In general, the ultrasonic transducer is a device which converts alternating current energy of 20 KHz or above to mechanical vibration of the same frequency using the piezoelectric effect or magnetostrictive effect. For example, the transducer includes a body with one open side and piezoelectric elements, the body is filled with air, and each piezoelectric element is connected with an electric wire to apply voltage. The piezoelectric element uses a material exhibiting a piezoelectric effect such as quartz and tourmaline, and the transducer generates and outputs ultrasound using the piezoelectric effect of the piezoelectric element. The outputted ultrasound forms a plane wave or a focused ultrasound beam according to the structure of the transducer.

As shown in FIG. 1, the focused ultrasound output unit 10 emits high intensity focused ultrasound (HIFU) to a target tissue T such as a fat cell or a tumor. A focal point position F is a point to which the output ultrasound beam is focused, and vibration energy by ultrasound converges on the single point to produce a strong nonlinear shockwave. Vapor bubbles of a few hundred μm to a few mm in size are formed at the focal point position F by the thermal effect of the shockwave (acoustic cavitation phenomenon), and as the bubbles vibrate and collapse/disappear, mechanical shocks are applied to the tissue. The characteristics of the output ultrasound differ depending on the output mode and it will be described in detail below.

The output characteristics of ultrasound differ depending on the output mode selected by the mode setting unit 20, and the direct control of the output characteristics of ultrasound according to the mode selection is performed by the control unit 30.

The existing ultrasound based lipolysis device does not actively control the output characteristics of ultrasound, and simply generates a predetermined level of thermal energy to burn off fats (about 65° C.). This method may have a risk of damaging the surrounding tissues (blood vessels, nerve cells, etc.) by heat dispersion, and it is difficult to predict the range and extent to which ultrasound breaks down fats and it is impossible to precisely remove only adipose tissues in a local area.

According to the proposed tissue removal device, it is possible to remove tissues (adipose tissues, tumor tissues, etc.) in a local area with high precision by controlling the output characteristics of focused ultrasound according to the mode selection. Hereinafter, three selectable output modes are described, but this is provided by way of example, and a variety of output modes may be added according to users' needs. Additionally, the term 'first', 'second' or the like is used to distinguish each output mode, and is not intended to indicate particular settings or the order of each mode.

In a first mode, the temperature in the tissue sharply rises using very high intensity focused ultrasound, and accordingly the tissue is removed using dynamic energy of formed vapor bubbles.

As opposed to the existing thermal ablation using thermal energy, this method mechanically removes the surrounding tissues by artificially generating cavitation through focused ultrasound. This technology also known as 'focused ultrasound soft tissue removal' or 'boiling histotripsy' forms vapor bubbles in a short time using ultrahigh intensity focused ultrasound having the acoustic pressure that is a few tens of times stronger than the existing method. Accordingly, it is possible to remove tissues in a shorter time than the existing method that ignites tissues by gradually increasing the temperature in the tissues, and monitor the treatment process in real time through cavitation monitoring.

Figure 2A:
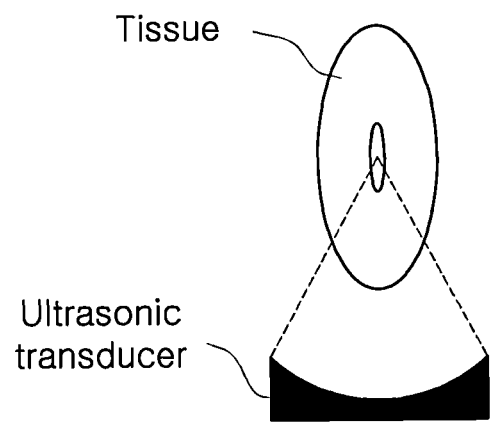
FIGS. 2A to 2E show a process of removing tissue using vapor bubbles formed by focused ultrasound.
Figure 2B:
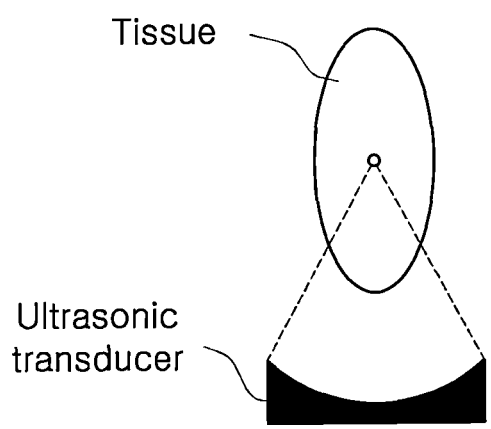
Figure 2C:
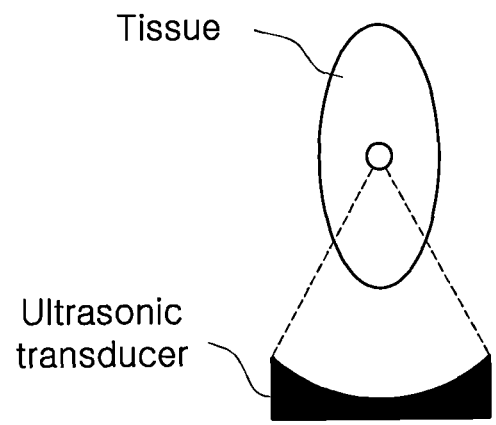
Figure 2D:
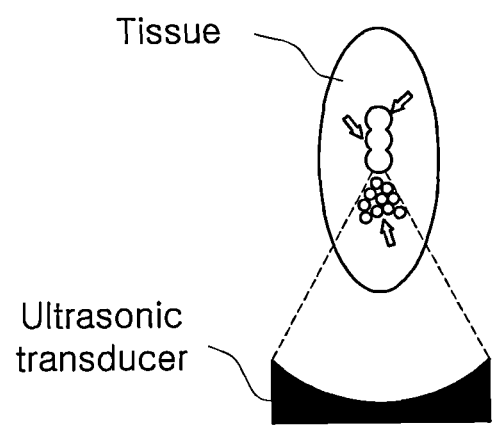
Figure 2E:
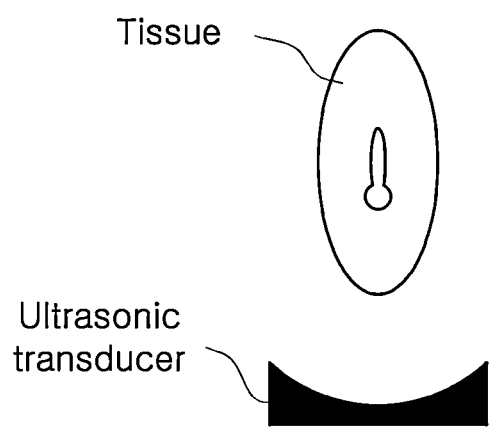

FIGS. 2A to 2E show a process of removing the tissue using vapor bubbles formed by focused ultrasound in the first mode. As shown, when high intensity focused ultrasound is outputted to a target tissue (lesion in an adipose tissue or a cancer cell) using the ultrasonic transducer, a shockwave is produced at the focal point of ultrasound (FIG. 2A), as water in the tissue is heated by the thermal effect of the shockwave, primary vapor bubbles are formed at the focal point (FIG. 2B), and the vapor bubbles grow by the rise in vapor pressure in the bubbles due to negative pressure (tension) that is longer than positive pressure (compression) in the nonlinear shockwave waveform and vapor introduced into the bubbles (FIG. 2C). The resulting bubbles form numerous secondary bubble clouds around the focal point by the shock scattering effect of ultrasound (FIG. 2D), and as the bubble clouds vibrate or collapse with changes in acoustic pressure, shocks are applied to the surrounding tissues (FIG. 2E).

According to an embodiment, in the first mode, the focused ultrasound is outputted with the center frequency of 0.1 to 30 MHz, and the pressure of the maximum positive pressure of 40 MPa or above and the maximum negative pressure of −10 MPa or below. Additionally, the pulse length may be 0.1 to 100 ms, the pulse repetition frequency may be 0.1 to 10 Hz, and the number of pulses may be one or more.

Figure 3A:
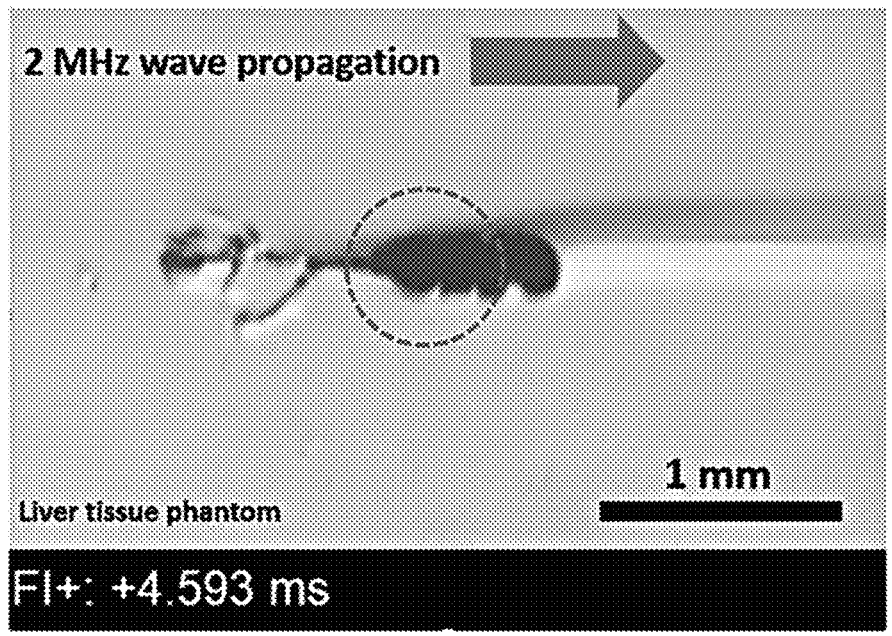
FIGS. 3A to 3C show experimental results of applying a focused ultrasound of an output mode to a tissue-mimicking gel according to an embodiment.
Figure 3B:
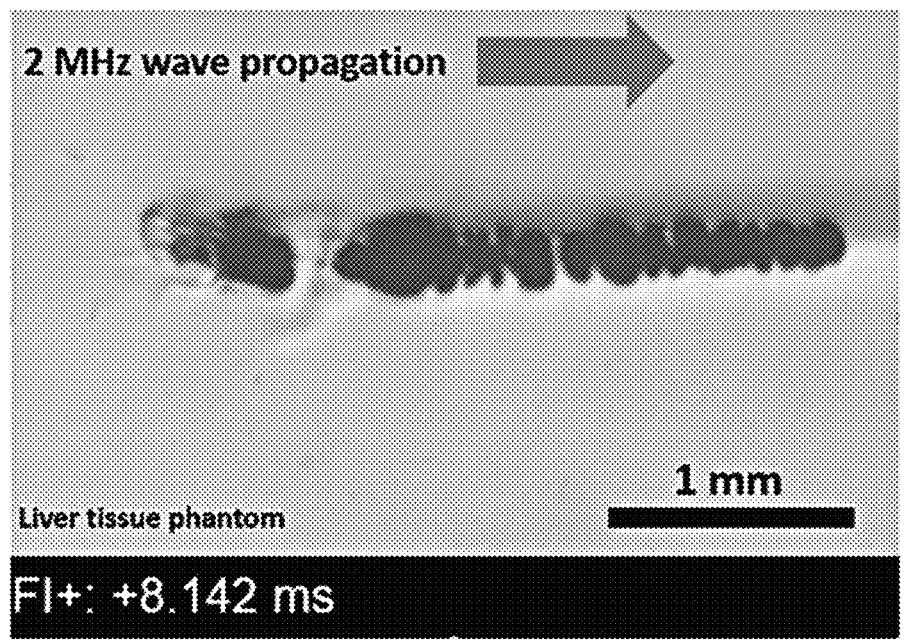
Figure 3C:
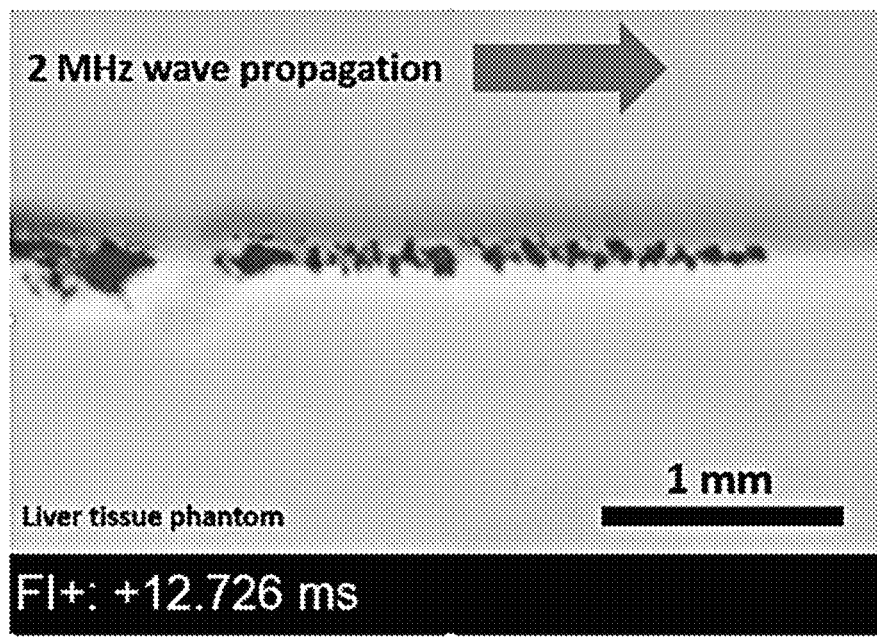

FIGS. 3A to 3C show the results of applying focused ultrasound according to the condition of the first mode to a tissue-mimicking gel. In the experimental example, an image is captured using a high speed camera (recording time is 0-13 ms) while emitting high intensity focused ultrasound having the fixed acoustic pressure of $P_+$=92 MPa, $P_-$=14 MPa and the frequency of 2 MHz to the tissue-mimicking gel for 10 ms. According to the simulation, the time required for the temperature of the gel to reach 100° C. is 3.84 ms. As shown, vapor bubbles are formed by an instantaneous temperature rise at the focal point position (indicated by the dashed circle) (FIG. 3A) and scattering bubble clouds are formed by the shock scattering effect (FIG. 3B). As the bubble clouds vibrate and collapse, mechanical shocks are applied to the tissue in the range of about 6-7 mm (FIG. 3C).

A second mode is selected when removing tissue in a narrower area than the first mode. In the second mode, the formation of bubble clouds by the shock scattering effect may be suppressed by controlling the output characteristics of ultrasound immediately after vapor bubbles are formed by focused ultrasound, thereby selectively removing tissue in a narrow area of 1-3 mm on the basis of the focal point position.

According to an embodiment, in the second mode, focused ultrasound is outputted in the same condition (the pressure of the maximum positive pressure of 40 MPa or above and the maximum negative pressure of −10 MPa or below) as the first mode for a predetermined time, and immediately after vapor bubbles are formed, is adjusted to the acoustic pressure of the lower maximum positive pressure of 40 MPa or below and maximum negative pressure of −10 MPa or above.

Figure 4A:
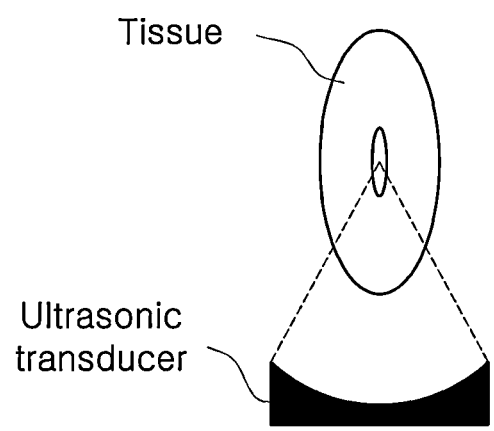
FIGS. 4A to 4C show a process of removing tissue in a local area by controlling the formation of vapor bubbles using pressure modulated focused ultrasound.
Figure 4B:
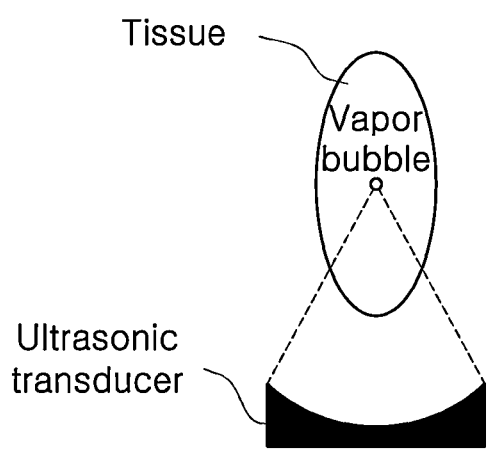
Figure 4C:
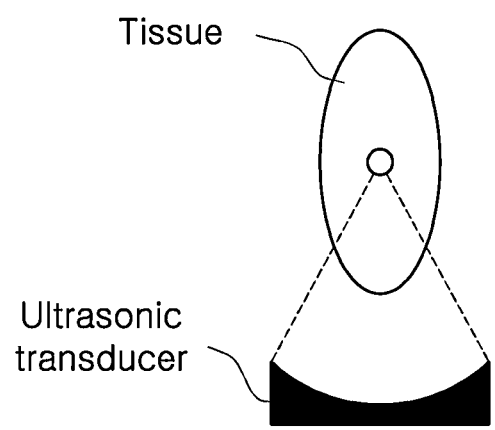

FIGS. 4A to 4C show a process of removing tissue in a local area by controlling the formation of vapor bubbles using pressure modulated focused ultrasound in the second mode. Referring to FIG. 4A, when high intensity focused ultrasound produces a strong shockwave at the focal point position, the temperature of the tissue rises due to the shockwave (the center frequency of ultrasound: 0.1-5 MHz). Alternatively, focused ultrasound having the pressure that is not high enough to produce a shockwave but the center frequency that is high enough to rapidly increase the temperature may be used (the center frequency of ultrasound: 5-30 MHz, in this case, the focal length may be shorter). Referring to FIG. 4B, when the temperature of water in the tissue increases, vapor bubbles are formed at the focal point position. Referring to FIG. 4C, when the vapor bubble formation or the temperature reaching the threshold is sensed, the control unit controls the intensity of focused ultrasound below the setting value. As a result, the shock scattering effect does not occur, consequential bubble clouds are not formed, and the removal area by the bubbles is limited to the focal point position.

Figure 5A:
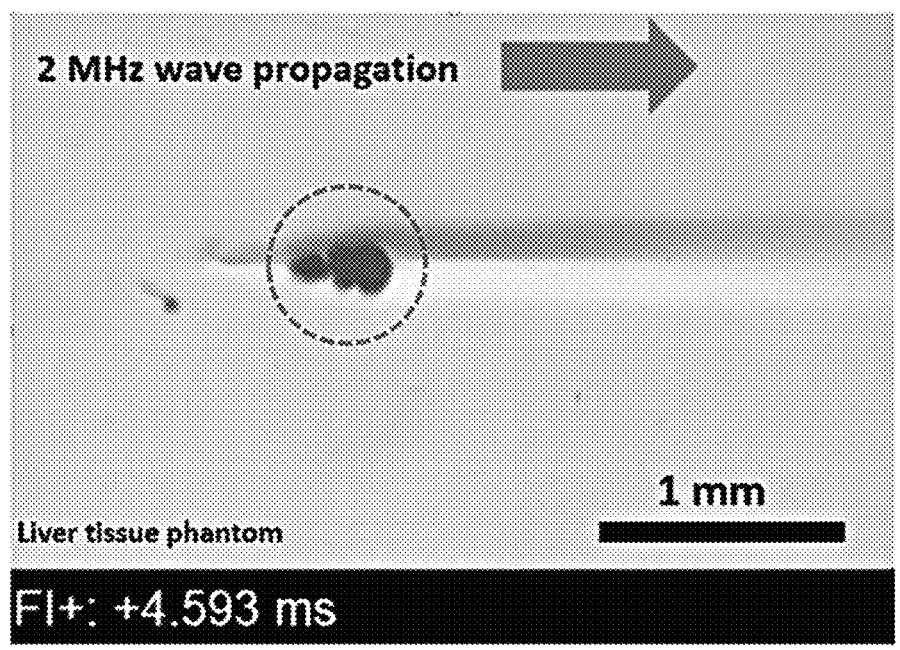
FIGS. 5A to 5C show experimental results of applying a focused ultrasound of an output mode to a tissue-mimicking gel according to another embodiment.
Figure 5B:
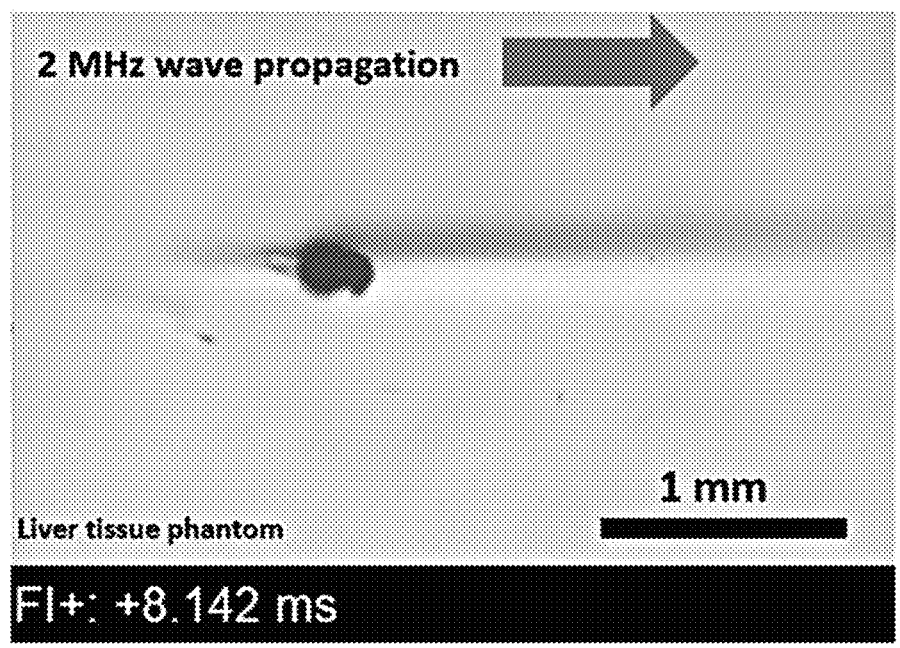
Figure 5C:
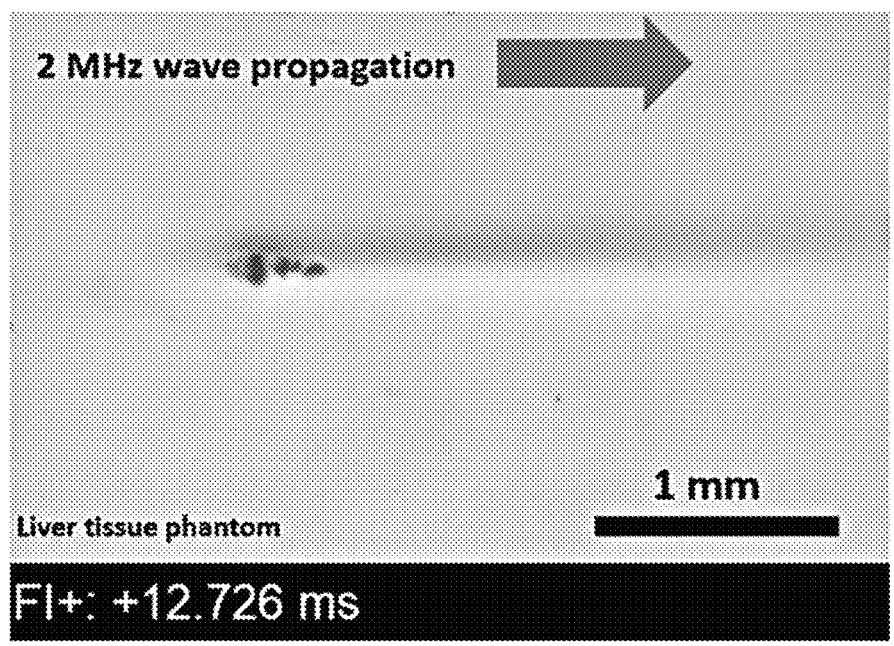

FIGS. 5A to 5C show the experimental results of applying focused ultrasound of the condition of the second mode to a tissue-mimicking gel. In the experimental example, from the beginning until vapor bubbles are formed, high intensity focused ultrasound of $P_+$=92 MPa, $P_-$=−14 MPa and the frequency of 2 MHz is emitted to the tissue-mimicking gel (the same condition as the first mode), and immediately after bubbles are formed, the acoustic pressure of ultrasound is adjusted to $P_+$=30 MPa, $P_-$=−9.4 MPa. As shown, vapor bubbles are formed at the focal point position (indicated by the dashed circle), but the shock scattering effect does not occur through the control of the ultrasound intensity (FIG. 5A), and accordingly, the formation of secondary bubble clouds is suppressed at other areas than the focal point position (FIG. 5B). As a result, shocks are only applied within the radius of 1 mm from the focal point position (FIG. 5C).

Data related to the output characteristics of focused ultrasound in the second mode and the time required to form vapor bubbles may be determined based on biomechanics information, thermodynamics information and bubble dynamics information. For example, in the experimental example of FIG. 5, the time point at which the output characteristics of ultrasound are controlled upon formation of vapor bubbles is about 3.84 ms, which is the calculated time required for the temperature at the focal point part to reach 100° C. when high intensity ultrasound having the frequency of 2 MHz and the acoustic pressure characteristics of the maximum positive pressure of 92 MPa and the maximum negative pressure of −14 MPa is outputted to the tissue (or a tissue-mimicking gel having similar physical properties) through simulation.

The rising temperature trend of the tissue by ultrasound and vapor bubble dynamics may be predicted using Bioheat transfer equation and Gilmore bubble equation. In other words, in a specific ultrasound irradiation condition (acoustic pressure, waveform, frequency and irradiation time of ultrasound), it is possible to predict information, for example, the time required for the focal point part to reach a specific temperature, the size of a vapor bubble that will be formed, and a motion change of the vapor bubble in a given acoustic field. It is possible to automatically control the intensity of ultrasound without a senor by inputting time information required to accomplish the condition beforehand.

According to another embodiment, the ultrasound pressure may be lowered at the moment at which vapor bubbles are formed while monitoring the vapor bubble formation time in the form of a signal/image using an additional ultrasonic sensor (or ultrasound imaging equipment) without pre-setting when to control the output characteristics of ultrasound.

According to the second mode setting, in the same way as the first mode, vapor bubbles are artificially formed using a strong nonlinear shockwave produced by the ultrasonic transducer, but a motion change of vapor bubble may be controlled by reducing the intensity of focused ultrasound below the set value by instantaneously changing the acoustic pressure and waveform of ultrasound when a specific condition (a preset time is reached or a vapor bubble is observed) is reached. After the control, the acoustic pressure of ultrasound is lower than the absolute pressure value at which the shock scattering effect occurs, so acoustic cavitation does not occur in other areas than vapor bubbles formed at the focal point of ultrasound. Accordingly, it is possible to precisely strike tissue (a fat cell or a tumor tissue) in a narrow area using only mechanical shocks generated by movement of predictable and controllable vapor bubbles.

In a third mode, heating is generated in the subcutaneous fat layer without directly damaging the tissue using focused ultrasound of lower intensity and longer pulse length than the first mode and the second mode. For example, in case that a fat cell is removed by ultrasound in the first mode or the second mode, the tissue density reduces and the skin layer sags or loses elasticity, and in the third mode, it is possible to obtain the body tightening effect that firms up the skin by tightening the skin tissues and regenerating collagen and elastin fibers by thermal energy using ultrasound having weak intensity and long pulse length.

Although the output characteristics and effects of ultrasound in the first to third output modes have been described, a variety of output modes may be added according to environments and purposes of use as described above.

Referring back to FIG. 1, the tissue removal device 1 according to an embodiment may include an ultrasound imaging unit 40 to monitor the formation of vapor bubbles and the tissue, and a display unit 50 to display an ultrasound image acquired by the ultrasound imaging unit.

The ultrasound imaging unit 40 may include a transducer to output high frequency imaging ultrasound and a computing device to create an ultrasound image based on the time for the ultrasound to bounce off the tissue and return. Using the ultrasound imaging unit 40, the focal point position of focused ultrasound may be detected or the presence or absence of cavitation may be monitored in real time. The display unit 50 outputs the ultrasound image acquired by the ultrasound imaging unit 40 in real time to allow the user to see the ultrasound image. The user can see the location of the target tissue, the focal point position of focused ultrasound and the presence or absence of a vapor bubble through the display unit 50.

According to an embodiment, the tissue removal device may further include a laser pointer (not shown) for marking the focal point position of focused ultrasound on the body surface. The orientation of the laser pointer matches the orientation of the ultrasonic transducer, and is set such that an intersection of a criss-cross laser pointer is placed on a straight line with the focal point position of focused ultrasound. It is possible to improve the surgical accuracy and convenience of the user by visually guiding the focus of focused ultrasound.

Figure 6:
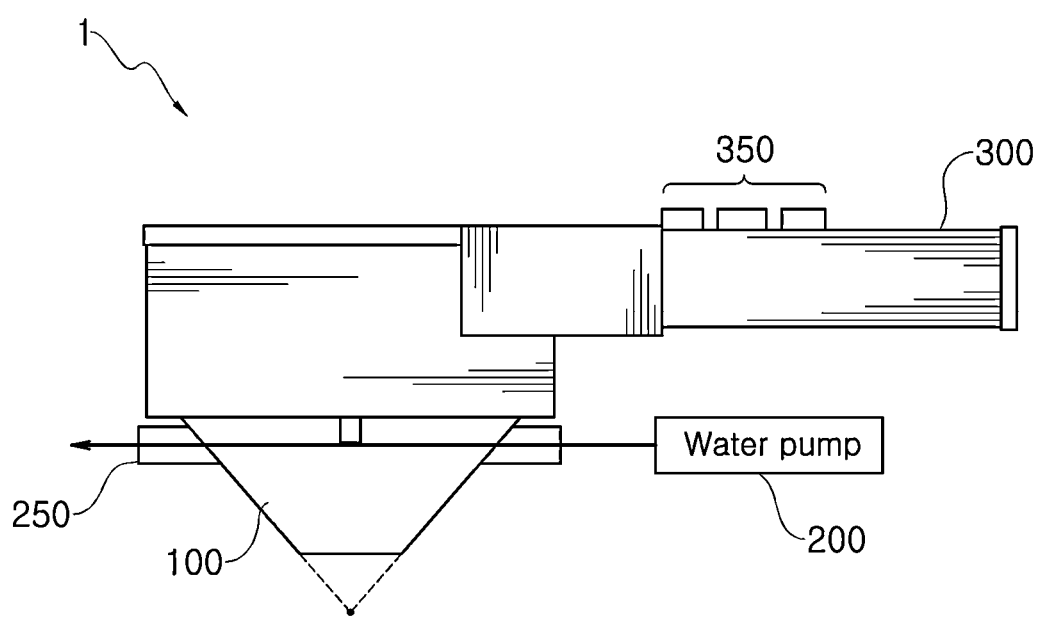
FIG. 6 shows a tissue removal device according to an embodiment when viewed from the side.

FIG. 6 shows the tissue removal device according to an embodiment when viewed from the side. The tissue removal device 1 is a hand-held device including a handle 300, and the handle 300 has an operation switch 350 for easy and simple output mode change and on/off.

According to an embodiment, the device may further include a multi-freedom compact operating system to enable fine-tuning of the focal point position of ultrasound without moving the focused ultrasound output unit, and the handle may further include a tuning switch used to fine-tune the position and angle of the focused ultrasound output unit through the multi-freedom compact operating system. The user can fine-tune the position and angle of the ultrasonic transducer through manipulation of the tuning switch attached to the handle while seeing the display.

Figure 7:
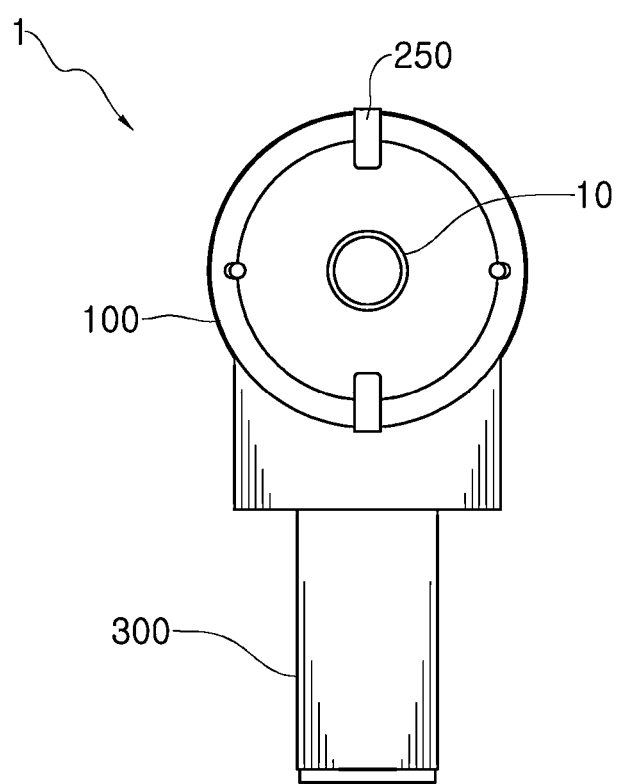
FIG. 7 shows a tissue removal device according to an embodiment when viewed from the top.

Referring to FIG. 6, the tissue removal device 1 includes an ultrasound guide unit 100 to support the focused ultrasound output unit (the transducer) and adjust the penetration depth of focused ultrasound, and the ultrasound guide unit 100 may be a structure having a water tube 250 through which water supplied through a water pump 200 passes. FIG. 7 shows the tissue removal device 1 according to an embodiment when viewed from the top.

Figure 8A:
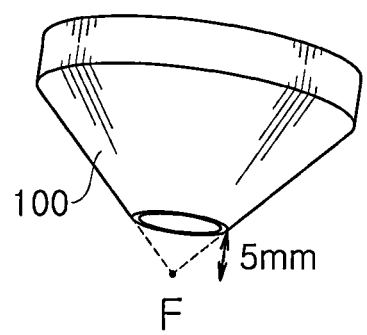
FIGS. 8A to 8C shows the penetration depth of focused ultrasound varying depending on the shape of an ultrasound guide unit according to an embodiment.
Figure 8B:
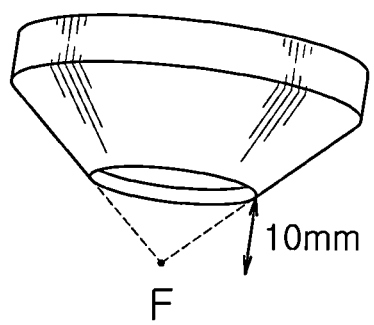
Figure 8C:
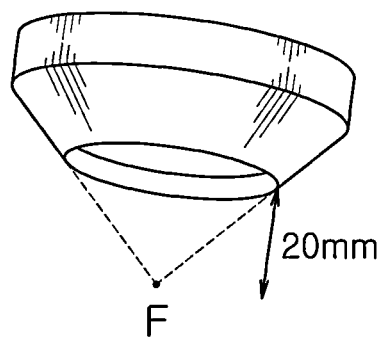

FIGS. 8A to 8C shows the ultrasound penetration depth varying depending on the shape of the ultrasound guide unit according to an embodiment. As shown, the ultrasound guide unit 100 has the shape of a truncated cone, and the truncation plane of the cone contacts the skin. Since ultrasound is focused onto the focal point position F, as the cone length of the guide unit is shorter, ultrasound is focused onto a deeper location in the body. In case that the focused ultrasound output unit includes an array of transducers, each having adjustable phase, it is possible to arbitrarily reduce or increase the focal length through phase control, but in case that the focused ultrasound output unit includes a single transducer, it is impossible to adjust the focal length at a fixed location. According to an embodiment, it is possible to adjust the focal length using a single transducer at a low price by replacing the ultrasound guide unit 100 of different shapes according to target focal point positions.

According to an embodiment, the ultrasound guide unit may be customized through 3D printing according to the user's body structure features.

According to an embodiment, the water pump 200 is configured to control the amount of water supplied to the ultrasound guide unit 100 based on the real-time ultrasound imaging results through the ultrasound imaging unit. The focal position of ultrasound may be changed by movement or breathing of a patient during treatment, and the change in focal point position of ultrasound may be compensated for by controlling the height of the ultrasound guide unit 100 by the control of the water pump amount according to the ultrasound imaging results as shown in an embodiment. To this end, the ultrasound guide unit 100 may be a variable structure that can expand or shrink with the introduction of water or an ultrasound gel.

According to the above-described acoustic cavitation based tissue removal device, it is possible to remove tissues, for example, adipose tissues in a non-invasive manner using high intensity focused ultrasound, and significantly reduce inflammation, swelling and blooding compared to the invasive method. Additionally, as opposed to the existing HIFU based devices, the acoustic cavitation based tissue removal device provides a variety of output modes, including the first mode for removing tissues in a relatively wide area using vapor bubbles formed by high intensity focused ultrasound, the second mode for selectively removing only tissues in a narrower area by reducing the ultrasound intensity using pressure modulated focused ultrasound at the moment at which vapor bubbles are formed, and the third mode for obtaining the body tightening effect using low intensity ultrasound. Additionally, it is possible to monitor the tissues and the formation of vapor bubbles (cavitation) in real time through ultrasound imaging. Accordingly, the user can remove tissues in a local area with high precision by controlling the output characteristics of focused ultrasound.

While the present disclosure has been hereinabove described with reference to the embodiments, it will be understood by those having ordinary skill in the corresponding technical field that various modifications and changes may be made to the present disclosure without departing from the spirit and scope of the present disclosure defined by the appended claims.

What is claimed is:

1. A cavitation based tissue removal device using focused ultrasound, comprising:
    a focused ultrasound output unit to output the focused ultrasound when a first mode or a second mode is selected;
    a mode setting unit to set an output mode of the focused ultrasound; and
    a control unit programmed to operate the focused ultrasound output unit in the first mode when the first mode is selected, and to operate the focused ultrasound output unit in the second mode when the second mode is selected,
    wherein, in the first mode, the control unit controls the focused ultrasound output unit to remove a tissue in a local area using a vapor bubble formed by the focused ultrasound,
    wherein, in the first mode, the control unit controls the focused ultrasound output unit such that the focused ultrasound forms scattered bubble clouds around the vapor bubble by a shock scattering effect,
    wherein, in the second mode, the control unit controls the focused ultrasound output unit to remove a tissue in a narrower area than the first mode by automatically controlling the output characteristics of the focused ultrasound immediately after the vapor bubble is formed by the focused ultrasound, and
    wherein, in the second mode, the control unit controls the focused ultrasound output unit such that the focused ultrasound only forms the vapor bubble in the tissue without forming the scattered bubble clouds by suppressing the shock scattering effect.

2. The cavitation based tissue removal device using focused ultrasound according to claim 1, further comprising:
    an ultrasound imaging unit to monitor the formation of the vapor bubble and the tissue; and
    a display unit to display an ultrasound image acquired using the ultrasound imaging unit.

3. The cavitation based tissue removal device using focused ultrasound according to claim 2, wherein the display unit is configured to display a focal point position of the focused ultrasound on the ultrasound image.

4. The cavitation based tissue removal device using focused ultrasound according to claim 1, further comprising:
    a laser pointer for marking a focal point position of the focused ultrasound on a body surface.

5. The cavitation based tissue removal device using focused ultrasound according to claim 1, wherein in the first mode, the focused ultrasound is controlled to have a frequency of 0.1 to 30 MHz, a pulse length of 0.1 to 100 ms, and a pressure of a maximum positive pressure of 40 MPa or above and a maximum negative pressure of −10 MPa or below.

6. The cavitation based tissue removal device using focused ultrasound according to claim 1, wherein the tissue includes a fatty tissue or a tumor tissue.

7. The cavitation based tissue removal device using focused ultrasound according to claim 1, further comprising:
    an ultrasound guide unit to support the focused ultrasound output unit and adjust a penetration depth of the focused ultrasound;
    a water pump to supply water to a water tube passing through the ultrasound guide unit; and
    a handle connected to the ultrasound guide unit and equipped with an operation switch to power on/off the device or select the output mode.

8. The cavitation based tissue removal device using focused ultrasound according to claim 7, further comprising:
    a multi-freedom compact operating system to enable fine tuning of a focal point position of the focused ultrasound without moving the focused ultrasound output unit,
    wherein the handle further includes a tuning switch used to fine-tune a position and angle of the focused ultrasound output unit through the multi-freedom compact operating system.

9. The cavitation based tissue removal device using focused ultrasound according to claim 7, wherein the ultrasound guide unit is customizable through 3D printing according to physical structure features of a user.

10. A cavitation based tissue removal device using focused ultrasound, comprising:
    a focused ultrasound output unit to output the focused ultrasound;
    a mode setting unit to set an output mode of the focused ultrasound; and
    a control unit to control output characteristics of the focused ultrasound according to the set mode,
    wherein the output mode is selected from:
    a first mode for removing a tissue in a local area using a vapor bubble formed by the focused ultrasound; and
    a second mode for removing a tissue in a narrower area than the first mode by controlling the output characteristics of the focused ultrasound immediately after the vapor bubble is formed by the focused ultrasound,
    wherein in the first mode, the focused ultrasound is controlled to have a frequency of 0.1 to 30 MHz, a pulse length of 0.1 to 100 ms, and a pressure of a maximum positive pressure of 40 MPa or above and a maximum negative pressure of −10 MPa or below, and
    wherein in the second mode, the focused ultrasound is outputted in a same pressure intensity condition as the first mode for a predetermined time, and immediately after the vapor bubble is formed, is controlled to have the pulse length of 1 to 100 ms and the pressure of the maximum positive pressure of 40 MPa or below and the maximum negative pressure of −10 MPa or above.

11. The cavitation based tissue removal device using focused ultrasound according to claim 10, wherein the predetermined time during which the focused ultrasound is outputted in the same condition as the first mode is set between 0.1 and 10 ms.

12. The cavitation based tissue removal device using focused ultrasound according to claim 10, wherein in the condition of the second mode, the focused ultrasound does not form a scattered bubble cloud in the tissue by a shock scattering effect.

13. The cavitation based tissue removal device using focused ultrasound according to claim 10, wherein in the condition of the second mode, the output characteristics of the focused ultrasound are at least determined based on biomechanics information, thermodynamics information and bubble dynamics information.

14. A cavitation based tissue removal device using focused ultrasound, comprising:
a focused ultrasound output unit to output the focused ultrasound;
a mode setting unit to set an output mode of the focused ultrasound; and
a control unit to control output characteristics of the focused ultrasound according to the set mode,
wherein the output mode is selected from:
a first mode for removing a tissue in a local area using a vapor bubble formed by the focused ultrasound; and
a second mode for removing a tissue in a narrower area than the first mode by controlling the output characteristics of the focused ultrasound immediately after the vapor bubble is formed by the focused ultrasound,
wherein the output mode further includes a third mode for tightening a skin without damaging the tissue by generating heating in a subcutaneous fat layer using the focused ultrasound of lower intensity and a longer pulse length than the first mode and the second mode.

15. A method for operating a cavitation based tissue removal device using focused ultrasound, the tissue removal device comprising a focused ultrasound output unit, a mode setting unit and a control unit, the method comprising:
receiving an input of selection of an output mode from a user between a first mode and a second mode;
setting the output mode of the focused ultrasound in response to the input; and
controlling output characteristics of the focused ultrasound to operate in the first mode when the first mode is selected and to operate in the second mode when the second mode is selected,
wherein, in the first mode, the focused ultrasound is controlled to remove a tissue in a local area using a vapor bubble formed by the focused ultrasound,
wherein, in the first mode, the focused ultrasound is controlled such that the focused ultrasound forms scattered bubble clouds around the vapor bubble by a shock scattering effect,
wherein, in the second mode, the focused ultrasound is controlled to remove a tissue in a narrower area than the first mode by automatically controlling the output characteristics of the focused ultrasound immediately after the vapor bubble is formed by the focused ultrasound, and
wherein in the second mode, the focused ultrasound is controlled such that the focused ultrasound only forms the vapor bubble in the tissue without forming the scattered bubble clouds by suppressing the shock scattering effect.

16. The method for operating a cavitation based tissue removal device using focused ultrasound according to claim 15, wherein the tissue removal device further comprises an ultrasound imaging unit and a display unit, and
the method for operating a cavitation based tissue removal device using focused ultrasound further comprises:
monitoring the formation of the vapor bubble and the tissue using the ultrasound imaging unit; and
displaying an ultrasound image acquired through the ultrasound imaging unit on the display unit.

17. A computer program stored in a non-transitory computer-readable recording medium, wherein the computer program includes instructions for performing a method for operating a cavitation based tissue removal device using focused ultrasound, the method comprising:
receiving an input of selection of an output mode from a user between a first mode and a second mode;
setting the output mode of the focused ultrasound in response to the input; and
controlling output characteristics of the focused ultrasound to operate in the first mode when the first mode is selected and to operate in the second mode when the second mode is selected,
wherein, in the first mode, the focused ultrasound is controlled to remove a tissue in a local area using a vapor bubble formed by the focused ultrasound,
wherein, in the first mode, the focused ultrasound is controlled such that the focused ultrasound forms scattered bubble clouds around the vapor bubble by a shock scattering effect,
wherein, in the second mode, the focused ultrasound is controlled to remove a tissue in a narrower area than the first mode by automatically controlling the output characteristics of the focused ultrasound immediately after the vapor bubble is formed by the focused ultrasound, and
wherein in the second mode, the focused ultrasound is controlled such that the focused ultrasound only forms the vapor bubble in the tissue without forming the scattered bubble clouds by suppressing the shock scattering effect.

* * * * *